United States Patent [19]

Baerns et al.

[11] Patent Number: 4,608,449
[45] Date of Patent: Aug. 26, 1986

[54] PROCESS FOR THE PRODUCTION OF ETHANE AND/OR ETHYLENE FROM METHANE

[75] Inventors: Manfred Baerns, Aeskulapweg 20, D-4630 Bochum, Fed. Rep. of Germany; Wilhelm Hinsen, Ratingen, Fed. Rep. of Germany

[73] Assignee: Manfred Baerns, Bochum, Fed. Rep. of Germany

[21] Appl. No.: 500,407

[22] Filed: Jun. 2, 1983

[30] Foreign Application Priority Data

Oct. 7, 1982 [DE] Fed. Rep. of Germany ....... 3237079

[51] Int. Cl.$^4$ .............................................. C07C 2/00
[52] U.S. Cl. ................... 585/500; 585/415; 585/417; 585/400; 585/541; 585/652; 585/658; 585/661; 585/943
[58] Field of Search ............... 585/500, 541, 943, 700, 585/652, 658, 400, 417, 661

[56] References Cited

U.S. PATENT DOCUMENTS

| | | | |
|---|---|---|---|
| 2,022,279 | 11/1935 | Feiler | 585/943 |
| 2,436,595 | 2/1948 | Nicholson et al. | 585/943 |
| 2,985,698 | 5/1961 | Pechtold et al. | 585/943 |
| 4,239,658 | 12/1980 | Mitchell et al. | 585/417 |
| 4,444,984 | 4/1984 | Jones et al. | 585/417 |

OTHER PUBLICATIONS

Fang et al., "Catalytic Pyrolysis of Methane", J. Chinese Chem Soc., 29, 265,273, 1981.
Keller and Bhasin, Synthesis of Ethylene via Oxidative Coupling of Methane, J. of Catalysts, 73, 9-19 (1982).

Primary Examiner—William R. Dixon, Jr.
Assistant Examiner—Cynthia A. Prezlock
Attorney, Agent, or Firm—Marshall, O'Toole, Gerstein, Murray & Bicknell

[57] ABSTRACT

Process and device for the production of ethane and/or ethylene by heterogeneous catalytic reaction of methane and oxygen using a catalyst suitable for the formation of $C_2$ hydrocarbons at increased temperatures, whereby in continuous operation a mixture of methane and oxygen is reacted at temperatures between 500° and 900° C. and at an oxygen partial pressure of less than 0.5 bar at the reactor entrance, while the ratio of the methane partial pressure to the oxygen partial pressure is greater than 1.

The conversion reaction takes place with or without gas recycling in a reactor containing a bed of solid catalyst or by the use of a fluidized bed of fluidized catalyst particles, or in a cross-flow reactor with distributed input of oxygen.

22 Claims, 3 Drawing Figures

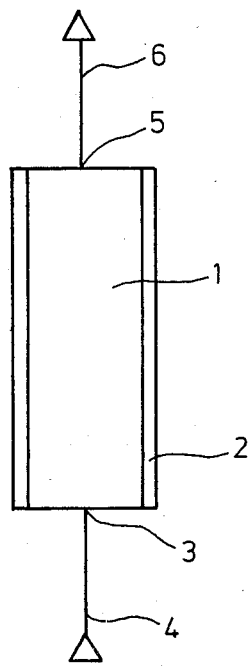
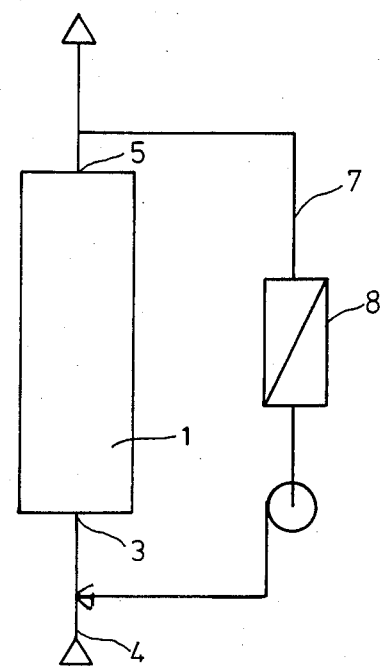
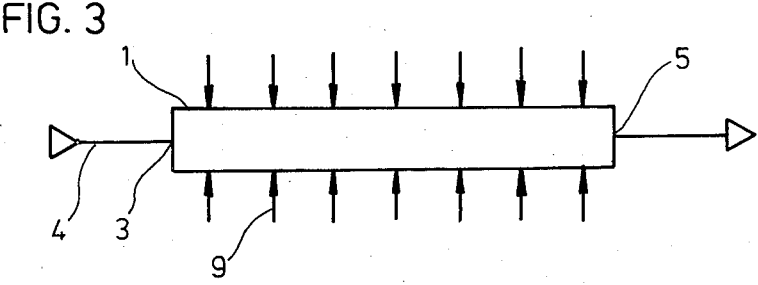

PROCESS FOR THE PRODUCTION OF ETHANE AND/OR ETHYLENE FROM METHANE

The invention concerns a process for the production of ethane and/or ethylene by the heterogeneous catalytic reaction of methane and oxygen using a catalyst suitable for the formation of $C_2$ compounds at increased temperatures.

Ethylene is one of the most important primary feedstocks for the organic and petrochemicals industries; today it is almost exclusively produced by the dehydrogenation of or the pyrolysis of ethane and propane, naphtha and in some cases from gas oil. Ethane and propane, which are contained in minor amounts in certain natural gas fields together with their main component methane, and thus available as natural raw materials in limited quantities for the production of ethylene.

Against this methane is available on a vast scale as natural gas. Particularly large amounts of methane are frequently found in the deep-lying oil fields; when the latter are exploited the methane is frequently flared of without use being made of its calorific or chemical raw material value.

The synthesis of higher hydrocarbons from methane is known from high temperature pyrolysis in electric arcs. But for thermodynamic reasons a dehydrogenating coupling of $CH_4$ only leads to very low yields of $C_2H_6$ and/or $C_2H_4$ as long as temperatures which are substantially more than 1000° C. are not used, as is technically realised in the so-called Hülser electric arc process. However this process is on the one hand exceptionally costly in power due to the high reaction temperatures required and on the other hand because of the high endothermicity of the reaction, so that it is not generally used.

German laid-open application 29 43 200 describes a process for the conversion of methane into ethane and/or ethylene, in which a mixture of chlorine and methane is converted at a molar ratio of methane to chlorine of from 1:1 to 10:1 at a temperature of at least 700° C. The gaseous chlorine which is converted in the reaction into hydrogen chloride serves as a possibly recyclable catalyst.

German laid-open specification 31 16 409 discloses a process for the manufacture of ethane from methane in which after adequate increase in temperature for a dissociative chemisorption, the catalytic surface is cooled to a temperature at which a C—C recombination takes place. The reaction is effected by using a platinum catalyst. Due to thermodynamic reasons this process does not yield sufficient yields of $C_2$ hydrocarbons.

To attain an optimal process it is necessary to achieve an especially high selectivity of the reaction as well as a high reaction rate; moreover the process used should be practicable at the lowest possible investment costs and should not have environmentally harmful effects. These preconditions are not optimally fulfilled when using the named processes.

Another possibility for the reaction of methane into higher hydrocarbons, i.e. in particular ethane and/or ethylene, consists of an oxidative coupling reaction of the methane. A corresponding reaction scheme is shown below.

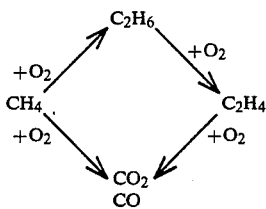

The energy required for the coupling of the methane to higher hydrocarbons is generated during the reaction itself, which moreover delivers additional energy.

The homogenous gas phase reaction between methane and oxygen however does not lead to $C_2H_6$ and/or $C_2H_4$ but to $CO_2$ and $H_2O$; the latter products are preferred thermodynamically.

G. E. Keller and M. M. Bashin (J. Catal.73,1982,9-19) have shown that in the presence of catalysts the reaction can be steered in the direction of the desired $C_2$ hydrocarbons: but the yields of ethylene plus ethane are low and amount to only 10% of the reacted methane. To improve the selectivity, i.e. to suppress the undesirable further reaction of the $C_2$ hydrocarbons formed into carbon oxides they therefore propose a special reaction method: the catalyst is first exposed to and loaded with oxygen by passing over it a gas containing oxygen; then in a second step, the gas phase oxygen in the catalytic reactor is supplanted by an inert gas before in the third step methane is passed over the catalyst which partially produces the desired reaction; in a fourth and last step an inert gas is again passed through the reactor to supplant the residual methane and the resulting product, before the first step begins anew. In this process depending on the catalyst used and the temperature selected, the selectivities for $C_2$ hydrocarbons amount to from 5 to 45% and for $CO_2$ correspondingly from 95 to 55% with conversions of methane between 1 and 10%.

Keller and Bashin arrive at the conclusion that the oxidative coupling is only highly selective to the higher hydrocarbons when the reaction takes place in the absence of gas phase oxygen. The oxidative coupling of the hydrocarbons should be caused by reaction with the lattice oxygen of the metal oxides, which are thus reduced by two valency stages. Since the lattice oxygen available in the catalyst is predetermined, for every unit of mass of the catalyst only a limited hydrocarbon quantity can be reacted.

It is evident that the modus operandi of Keller and Bashin is costly in terms of apparatus as well as being simultaneously linked with small yields in space-time terms and high operating and investment costs. Moreover the attainable methane conversions and/or the resultant space-time yields are too small for a commercial installation according to the data of the authors.

The invention is based on the object of making available a process for the production of ethane and/or ethylene from methane by the oxidative coupling system, which allows especially good selectivities and conversions, and wherein additionally the investment costs are low and an unfavorable influence on the environment is avoided.

This object is attained according to the invention by means of the process named above, wherein in continuous operations a mixture of methane and oxygen is reacted at temperatures between 500° C. and 900° C.

and at an oxygen partial pressure of <0.5 bar at the reactor entrance, while the ratio of the methane partial pressure to oxygen partial pressure is >1.

Contrary to the conclusions which can be derived from the experiments made by Keller and Bashin, i.e. that to attain higher selectivities a periodic process is necessary, it is surprisingly found when using the inventive process that without such a complicated and costly process as that of Keller and Bashin, comparable and to some extent better selectivities are obtained with, in particular, higher space-time yields of $C_2$ hydrocarbons.

In the inventive process a mixture of methane and of oxygen which can also contain insert gas shares, such as nitrogen for example, is passed at temperatures between 500° and 900° C., preferably between 600° and 800° C., over a catalyst.

The methane partial pressure at the reactor entrance should be kept as high as possible, and should amount to at least 0.2 to 1 bar. The methane partial pressure may also be above 1 bar.

On the other hand the oxygen partial pressure must be comparatively low; it should have a value of <0.5 bar. It is preferable when the oxygen partial pressure amounts to 0.02 to 0.2 bar, and especially preferred when this amounts to 0.04 to 0.12 bar.

In addition the residence time of the reagents in the reactor should be chosen so that the oxygen partial pressure at the reactor exit tends towards zero.

The ratio of methane partial pressure to oxygen partial pressure should be <1, and preferably should have the value 2 to 10.

In principle there are no limits to the total pressure upwards in the process according to the invention.

Depending on the chosen reaction conditions, the catalytic conversion reaction is carried out in a catalytic fixed bed reactor, a cross-flow reactor or in the presence of a fluidized catalyst in a fluidized bed reactor. It is also advantageous to use a multi tube reactor.

When using a catalytic fixed bed reactor through which reaction gas passes in a one-time or repeated passage, selectivities with respect to the $C_2$ hydrocarbons of more than 50% are achieved. A useful improvement of the selectivity can be attained if the reactor is not operated with one-time passage, but with gas recycling, i.e. using repeated through-put, in order to keep the concentration of oxygen low. The higher the ratio of recycled gas volume to fresh gas volume per time unit, the higher is the selectivity which results. The operation conditions should be arranged in such a way that the oxygen introduced by the fresh gas is converted as completely as possible. It is preferable for a part of the reaction mixture which leaves the reactor to be recycled as recycle gas to the reactor entrance, in order to be recycled with the fresh gas consisting of methane and oxygen as well as optionally an inert gas component.

It is advantageous to adjust the ratio of recycle gas volume to fresh gas volume to at least 1, and a special preference is given to from 10 to 20.

It is expedient to separate the $C_2$ hydrocarbons and the higher hydrocarbons and optionally $CO_2$ and $H_2O$ possibly formed from the gas to be recycled in a suitable separation device.

A further modification of the inventive process which also leads to excellent results consists of the use of a fluidized bed of fluidized catalyst particles which is fluidized by reaction gas.

A further reaction technology possibility for the attainment of a high $C_2$ selectivity which allows the application of low oxygen partial pressures together with high reaction rates, is provided by the cross flow reactor; oxygen is fed in along the reactor in such a manner that its partial pressure in the reactor remains below 0.1 bar.

As the catalyst, any catalyst suitable for the formation of higher hydrocarbons from methane or for the formation of $C_2$ hydrocarbons is employed. It is especially preferable to choose a catalyst from the group of the metal oxides. Particularly suitable are the oxides of the groups III–VII of the periodic system. Special preference is given to catalysts of lead oxide, manganese oxide, antimony oxide, tin oxide, bismuth oxide, thallium oxide and indium oxide. The greatest preference is given to lead oxide. Equally mixtures of the named metal oxides have a catalytic effect.

The metal oxides can be used with and without carrier material. Specially preferred carrier materials are $Al_2O_3$, $SiO_2$ and $TiO_2$ as well as further suitable inert oxides.

A specially suitable catalyst/carrier substance is $PbO/Al_2O_3$. Advantageously mixed catalysts are $PbO/Bi_2O_3/Sb_2O_3$.

The course of the process for the three reaction engineering variants:

(a) reactor without gas recycling,
(b) reactor with gas recycling, and
(c) reactor with distributed oxygen addition (cross flow reactor) is shown schematically in FIGS. 1 to 3, in which FIG. 1 shows variant (a),
FIG. 2 shows variant (b), and
FIG. 3 shows variant (c).

In detail the reference numerals in FIGS. 1 to 3 indicate: 1 a reactor, 2 a heat exchanger, 3 the reactor entrance, 4 a feed line of methane or for the mixture methane/oxygen fitted with a pressure gauge as well as a dosing valve, 5 is the rector exit with an outlet line 6, 7 to a recycle line from the reactor exit 5 to the reactor entrance 3, 8 is a separation device for separation of the higher hydrocarbons as well as optionally $CO_2$ and $H_2O$ from the recycle gas, and 9 are leads along the reactor tube for the injection of oxygen or oxygen+inert gas.

In the following examples the reactor was supplied with variously mixed gas flows of methane, synthetic air and nitrogen via the gas supply.

The gas dosing is effected by needle valves, the volume flow measurement is done by capillary flow meters. At the reactor inlet the pressure drop is measured by a manometer. The pressure in the reactor, which was almost the same as the external pressure, resulted from the flow resistance of the pipelines and the filling. To avoid catalytic wall reactions, the cylindrical reactor was made of quartz; its internal diameter was 0.6 cm., its jacketed length was 9 cm. Thermostabilisation was performed by a heating block surrounding the reactor made of metal. The catalysts with a particle size of from 0.25 to 0.5 mm were held on a quartz filling in the reaction zone. To exclude largely any temperature gradients in the filling, the catalysts in some of the tests were diluted with quartz of the same grain size. Temperature measurement was carried out directly in the catalyst filling by a thermoelement movably inserted in a quartz jacket.

The reaction gas leaving the reactor was led into a heated pipeline and supplied to a gas chromatograph with two 6-way valves with a 0.1 ml sample loop, as the sampling valve. Before the second unheated sampling valve, the reaction water was condensed out in two consecutive cooling traps. In the first, using columns packed with carbosieve S, $O_2$, $N_2$, CO, $CH_4$, $C_2H_4$, $C_2H_6$ and $C_3H_8$ were separated and quantitatively determined using a combination of a thermal conductivity detector (WLD) and a flame isolation detector (FID). Considering the volume change by the condensation of the reaction water, in the second column packed with Porasil C the $CO_2$ was determined using a WLD; by the use of a connected FID the $C_2$ to $C_4$ hydrocarbons could again be analysed for control purposes. Sample tests were made of the separated reaction water for possibly formed formaldehyde with a solution of 5% hydroxylammonium chloride in water and titration of the hydrochloric acid released with 0.1 NaOH.

The catalysts used in the tests differ as to their preparation process, as shown in the examples of catalyst preparation.

In general the freshly prepared catalysts were dried for several hours at 120° C. in a vacuum and then calcinated over night at 600° to 700° C. Powdery material was pelletized and then crushed as were the solids caked together during calcination to from 0.25 to 0.5 mm.

EXAMPLES OF CATALYST PREPARATION

The catalysts used according to the invention were prepared as follows:

(a) $PbO/Al_2O_3$ (35% PbO by weight)

Using a solution of 6.06 g, $PbO(NO_3)_2$ in 25 ml water 11.6 g of powdery $\gamma$-$Al(OH)_3$ were suspended and thickened into a paste while stirring at 80° C. This was dried for 5 h at 120° C. in water jet pump vacuum. During the subsequent calcination within 3.5 h the temperature was raised to 500° C. and kept there for 1 h. The final calcination was effected at 600° C. for 14 h.

(b) $PbO/Al_2O_3$ (34% by weight of PbO)

A solution of 3.9 g $Pb(NO_3)_2$ in 11.5 ml water was added to 5.12 g $\gamma$-$Al_2O_3$ (BET surface 160 m$^2$/g, average mesopore radius 4.9 nm) and the suspension was stirred for 1.5 h. At 80° C. the water was evaporated in water jet pump vacuum and then dried for 16 h at 160° C.

For calcination heating was effected within 3 h to 500° C. and then the temperature was raised to 600° C. for 17 h.

(c) $PbO/SiO_2$ (43% by weight PbO)

22.9 g $Pb(NO_3)_2$ were dissolved in 35 ml water at boiling point. 20.5 g silica gel (grain size 0.2 to 0.5 mm) were added to the boiling solution. The suspension was further heated while stirring until after 30 minutes the residual fluid had a gelatinous consistency. After cooling there was a still moist solid present, which was dried in a water jet pump vacuum at 80° C. For calcination heating was effected to 600° C. in 3 h, and this temperature was maintained for 14 h.

(d) $PbO/Bi_2O_3$ (12% by weight of PbO)

Crystalline $Bi(NO_3)_3.5H_2O$ was first heated for 1 h in vacuum to 110° C., while the crystallization water was given off. For decomposition of the nitrate to $Bi_2O_3$ heating was effected to 280° C. in the water jet pump vacuum. To a screening fraction of 0.25 to 0.5 mm of the $Bi_2O_3$ thus prepared (6.22 g) 1.31 g $Pb(NO_3)_2$ were added in 15 ml water and stirred for 2 h at room temperature. The drying was carried out firstly at 50° C. for 16 h, then for 6 h at 120° C. in a vacuum. Calcination was performed for 16 h at 700° C.

(e) $Bi_2O_3$—$SnO_2$ ($SnO_2:Bi_2O_3 = 57:43$)

19.4 g $Bi(NO_3)_3.5H_2O$ were suspended in 300 ml water (with subsequent pH=0.5). Using concentrated $NH_3$(aq) titration was effected to pH=7 and then by simultaneous dripping of $NH_3$(aq) in 200 ml water, the dissolved $SnCl_4$ (22.1 g) was precipitated at pH=7. The solids were filtered off and washed free of chloride. After 2 h drying at 120° C. calcination was carried out for 16 h at 700° C. in the water jet pump vacuum.

(f) $SnO_2$ 44.3 g $SnCl_4$ were dissolved in 150 ml water and precipitated by the simultaneous addition of $NH_3$(aq) at pH=7. After filtering off and washing out the chloride drying was carried out over night at 100° C. in a vacuum. Calcination took place at 700° C. for 16 h.

(g) $PbO$—$Bi_2O_3$—$Sb_2O_3$ ($PbO:Bi_2O_3:Sb_2O_3 = 31:54:14$) Initial Components PbO was produced by the decomposition of $Pb(NO_3)_2$ for 3 h at 580° C. and was ground to powder.

$Bi_2O_3$ was prepared by heating crystalline $Bi(NO_3)_3.5H_2O$ for 1 h to 110° C. in a vacuum and decomposition of the nitrate at 280° C. for 60 h in a vacuum, and was ground to powder.

$Sb_2O_3$ was used as a powder in the form usual in the trade.

A suspension of PbO (5.09 g), $Bi_2O_3$ (8.58 g) and $Sb_2O_3$ (2.24 g) was stirred in 13 ml water at room temperature for 18 h, and then with continued stirring during heating to ca. 50° C. the water was evaporated until a paste formed. After drying for 16 h at 120° C. in a vacuum the metal oxide mixture was calcinated for 16 h at 700° C.

(h) $Sb_2O_3/SnO_2$ ($Sb_2O_3:SnO_2 = 35:65$)

A suspension of 10.4 g $SbCl_3$ in a solution of 22.1 g $SnCl_4$ was dripped in 100 ml distilled water with simultaneous addition of $NH_3$ (aq) in a receiver tank of 1000 ml water with a pH=7 being maintained. The deposit was filtered off. After 3 h drying in vacuum at 120° C. it was calcinated for 14 h at 700° C.

(i) $Mn_xO_y/Al_2O_3$ (27% by weight Mn as $MnO_2$)

9.94 g $Mn(NO_3)_2.4H_2O$ were dissolved in 20 ml water. After the addition of 10.4 g $\gamma$-$Al_2O_3$ (BET surface 160 m$^2$/g average mesopore radius 4.9 nm) water was evaporated while stirring at 60° C. until a paste formed. Drying took place for 16 h at 40° C. in a vacuum; then for 2 h at 120° C. Calcination was performed at 700° C. for 18 h.

Below the embodiments 1 to 10 of the inventive process are cited. Examples 1 to 9 describe the process using a catalytic solid bed reactor without gas recycling and example 10 shows the process in a catalytic solid bed reactor with gas recycling. The difference in the results with and without gas recycling emerges from the comparison of examples 9 and 10. It is seen that using the process of the invention with gas recycling, the selectivity is almost doubled against the process in the solid bed reactor without gas recycling, in a surprising way.

EXAMPLES 1 TO 9

A mixture of methane and oxygen to which for reasons of exact gas dosing and analysis, nitrogen has been added, is passed in a straight one-time through-put over the catalyst arranged in a tubular reactor. The catalysts used were the materials cited in the above examples of catalyst preparation.

By adding inert material to the reactor, it can be largely operated isothermally under reaction conditions. The gases leaving the reactor are analysed gas chromatographically for methane, the olefin and paraffin $C_2$ to $C_4$ hydrocarbons, as well as $O_2$, CO, $CO_2$ and $N_2$ after separation of the reaction water formed.

The conditions used for the exemplary tests 1 to 9 are listed in Table 1. They include the partial pressures of methane $p°_{CH_4}$ and oxygen $p°_{O_2}$ at the reactor entrance, the reaction temperature T and the gas through put F/W based on the catalyst amount. The results obtained are cited in the form of the oxygen partial pressure at the reactor exit $p_{O_2}{}^e$ and the selectivities $S_i$ determined for the $C_2$ to $C_3$ hydrocarbons formed. The selectivity $S_i$ of a hydrocarbon with i carbon atoms is defined as follows:

$$S_i = \frac{|\nu_1| n_{C_i}}{n°_{CH_4} - n_{CH_4}} \cdot 100\%$$

where $n_{C_i}$ is the number of the moles formed of the hydrocarbon with i carbon atoms, $(n°_{CH_4} - n_{CH_4})$ is the number of reacted moles of methane and $\gamma_i$ is the stoichiometric reaction number:

$$\gamma_i CH_4 + yO_2 \rightarrow C_iC_{2i}(\text{or } C_iH_{2i+2}) + xH_2O.$$

The results of examples 1 to 9 are summarized in Table 1.

TABLE 1

Experimental Conditions and Results of Embodiments 1 to 9

| EXAMPLE | 1 | 2 | 3 | 4 | 5 | 6 | 7 | 8 | 9 |
|---|---|---|---|---|---|---|---|---|---|
| Catalyst | $PbO/Al_2O_3$ (I) | $PbO/Al_2O_3$ (III) | $PbO/Bi_2O_3$ | | $PbO/Bi_2O_3$ | | $PbO/Bi_2O_3$ $Sb_2O_3$ | $PbO/Al_2O_3$ (III) | |
| $p_{CH_4}{}^o$ bar | 0.32 | 0.46 | 0.25 | 0.26 | 0.24 | 0.25 | 0.47 | 0.51 | 0.50 |
| $p_{O_2}{}^o$ bar | 0.062 | 0.052 | 0.10 | 0.052 | 0.05 | 0.041 | 0.033 | 0.052 | 0.10 |
| T °C. | 657 | 656 | 700 | 700 | 697 | 697 | 698 | 751 | 651 |
| F/W $\frac{ml}{s\ g^{-cat.}}$ | 1.2 | 1.6 | 4.2 | 4.1 | 0.1 | 0.05 | 0.115 | 23.4 | 5.61 |
| $p_{O_2}{}^e$ bar | 0 | 0 | 0.004 | 0.002 | 0.028 | 0.006 | 0.002 | 0.002 | 0.009 |
| $S_{C_2H_4}$ % | 9.6 | 7.0 | 10.7 | 12.2 | 4.4 | 14.6 | 5.1 | 11.2 | 3.1 |
| $S_{C_2H_6}$ % | 21.1 | 30.7 | 14.5 | 26.2 | 26.4 | 31.8 | 39.7 | 41.1 | 14.4 |
| $S_{C_3H_8}$ % | n.b.[1] | n.b.[1] | 0.2 | 0.3 | — | 0.7 | 0.3 | 0.6 | 0.4 |
| $\Sigma S_i$ % | 30.7 | 37.7 | 25.4 | 38.7 | 30.8 | 47.1 | 45.1 | 52.9 | 17.9 |

[1]not determined

EXAMPLE 10

For this example PbO was used as the active catalyst component on an $Al_2O_3$ carrier. Reaction temperature was 650° C. For the fresh gas through-put F/W based on the amount of catalyst a value of 2.3 ml/s g-catalyst was used. The partial pressures at the reactor entrance amounted to 0.51 bar for methane and to 0.1 bar for oxygen. A part of the reaction gas leaving the reactor was recycled to the reactor entrance; the ratio of the recycle gas volume to fresh gas volume amounted to about 20. All the other conditions as well as the analysis and selectivity determinations corresponded to the examples 1 to 9 above. The selectivity achieved for ethane was 28.2% and the ethylene it was 3.9%. The oxygen partial pressure at the reactor exit was about 0.01 bar.

We claim:

1. In a process for the production of ethane and/or ethylene by heterogeneous catalytic reaction of methane and oxygen carried out in the presence of a suitable catalyst of the type exemplified by lead oxide, manganese oxide, antimony oxide, tin oxide, bismuth oxide, cadmium oxide, thallium oxide and indium oxide or mixtures thereof and optionally in the presence of a suitable catalyst carrier of the type exemplified by aluminum oxide ($Al_2O_3$), silica ($S_iO_2$) and titania ($T_iO_2$), the improvement comprising performing the reaction continuously at temperatures between 500° C. and 900° C. at oxygen partial pressures of less than 0.5 bar at the reactor entrance, wherein the ratio of the methane partial pressure to the oxygen partial pressure is greater than one.

2. A process according to claim 1, characterized in that the reaction takes place at a temperature of from 600° C. to 800° C.

3. A process according to claim 1 or 2, characterized in that the methane partial pressure at the reactor entrance is 0.2 to 1 bar.

4. A process according to claim 1, characterized in that the oxygen partial pressure at the reactor entrance is 0.02 to 0.2 bar.

5. A process according to claim 4, characterized in that the oxygen partial pressure at the reactor entrance is 0.04 to 0.12 bar.

6. A process according to claim 1, characterized in that the residence time of the reagents in the reactor is chosen so that the oxygen partial pressure at the reactor exit tends towards zero.

7. A process according to claim 1, characterized in that the ratio of the methane partial pressure to the oxygen partial pressure is 2 to 10.

8. A process according to claim 1, characterized in that the mixture of methane and oxygen can also contain inert gas shares.

9. A process according to claim 8, characterized in that the mixture of methane and oxygen can contain nitrogen, carbon dioxide or water.

10. A process according to claim 1, characterized in that the conversion reaction takes place in a catalytic fixed bed reactor or in a catalytic fixed bed multi tube reactor.

11. A process according to claim 10, characterized in that for the conversion the reacting gas mixture is passed through the catalytic fixed bed reactor or multi tubular catalytic fixed bed reactor in a one-time or repeated pass.

12. A process according to claim 1, characterized in that the conversion takes place in the presence of a catalyst fluidized in a fluidized bed reactor.

13. A process according to claim 10 or 12, characterized in that a part of the reaction mixture, which leaves the reactor, is returned as recycle gas to the reactor entrance and is recycled together with the fresh gas consisting of methane and oxygen into the reactor.

14. A process according to claim 10 or 12, characterized in that a part of the reaction mixture, which leaves the reactor, is returned as recycle gas to the reactor entrance and is recycled together with the fresh gas consisting of methane, oxygen and an inert gas component into the reactor.

15. A process according to claim 13, characterized in that the ratio of recycle gas volume to fresh gas volume is at least 1.

16. A process according to claim 14, characterized in that the ratio of recycle gas volume to fresh gas volume is at least 1.

17. A process according to claim 13, characterized in that the ratio of recycle gas volume to fresh gas volume is from 10 to 20.

18. A process according to claim 14, characterized in that the ratio of recycle gas volume to fresh gas volume is from 10 to 20.

19. A process according to claim 1, characterized in that the methane is fed to the reactor entrance while the oxygen is fed along the direction of flow of the reaction gas laterally into the reactor so that the oxygen partial pressure arising in the reactor is 0.02 to 0.2 bar.

20. A process according to claim 1, characterized in that the methane is fed to the reactor entrance while the oxygen in the presence of an inert gas component is fed along the direction of flow of the reaction gas laterally into the reactor so that the oxygen partial pressure arising in the reactor is 0.02 to 0.2 bar.

21. A process according to claims 11, 19 or 20 characterized in that hydrocarbons with a carbon number greater than one are separated from the recycle gas before it is recycled into the reactor.

22. A process according to claims 11, 19 or 20 characterized in that hydrocarbons with a carbon number greater than one as well as $CO_2$ and $H_2O$ are separated from the recycle gas before it is recycled into the reactor.

* * * * *